(12) United States Patent
Webb

(10) Patent No.: US 8,630,714 B1
(45) Date of Patent: Jan. 14, 2014

(54) BONE GROWTH STIMULATION USING A CONSTANT CURRENT CAPACITIVELY COUPLED STIMULATOR

(75) Inventor: Douglas E. Webb, Venice, FL (US)

(73) Assignee: Electrostim Medical Services, Inc., Tampa, FL (US)

( * ) Notice: Subject to any disclaimer, the term of this patent is extended or adjusted under 35 U.S.C. 154(b) by 131 days.

(21) Appl. No.: 12/495,433

(22) Filed: Jun. 30, 2009

Related U.S. Application Data

(60) Provisional application No. 61/133,785, filed on Jun. 30, 2008, provisional application No. 61/076,991, filed on Jun. 30, 2008.

(51) Int. Cl.
*A61N 1/00* (2006.01)

(52) U.S. Cl.
USPC ............................................................ 607/51

(58) Field of Classification Search
USPC .................................. 607/51–53, 4
See application file for complete search history.

(56) References Cited

U.S. PATENT DOCUMENTS

| | | | | |
|---|---|---|---|---|
| 4,467,809 A | * | 8/1984 | Brighton | 607/51 |
| 5,584,863 A | * | 12/1996 | Rauch et al. | 607/2 |
| 7,117,034 B2 | * | 10/2006 | Kronberg | 607/2 |
| 2002/0052634 A1 | * | 5/2002 | March | 607/50 |
| 2003/0191510 A1 | * | 10/2003 | Ochs et al. | 607/62 |
| 2004/0015209 A1 | * | 1/2004 | McGraw et al. | 607/51 |
| 2006/0025825 A1 | * | 2/2006 | Bowers | 607/5 |
| 2009/0182389 A1 | * | 7/2009 | Stessman | 607/11 |

* cited by examiner

*Primary Examiner* — George Manuel
*Assistant Examiner* — Minh Duc Pham
(74) *Attorney, Agent, or Firm* — Workman Nydegger

(57) ABSTRACT

A non-invasive bone growth stimulation system and method of use are disclosed. The non-invasive bone growth stimulation system generates a substantially constant AC current signal that is delivered to a body to treat bone fractures. The substantially constant AC current is derived from a square wave that is converted to a sinusoidal signal with at least one low pass filter to effectively produce the constant AC current at the fundamental frequency of the square wave.

20 Claims, 13 Drawing Sheets

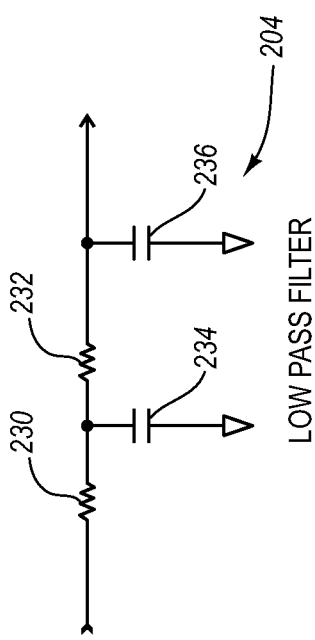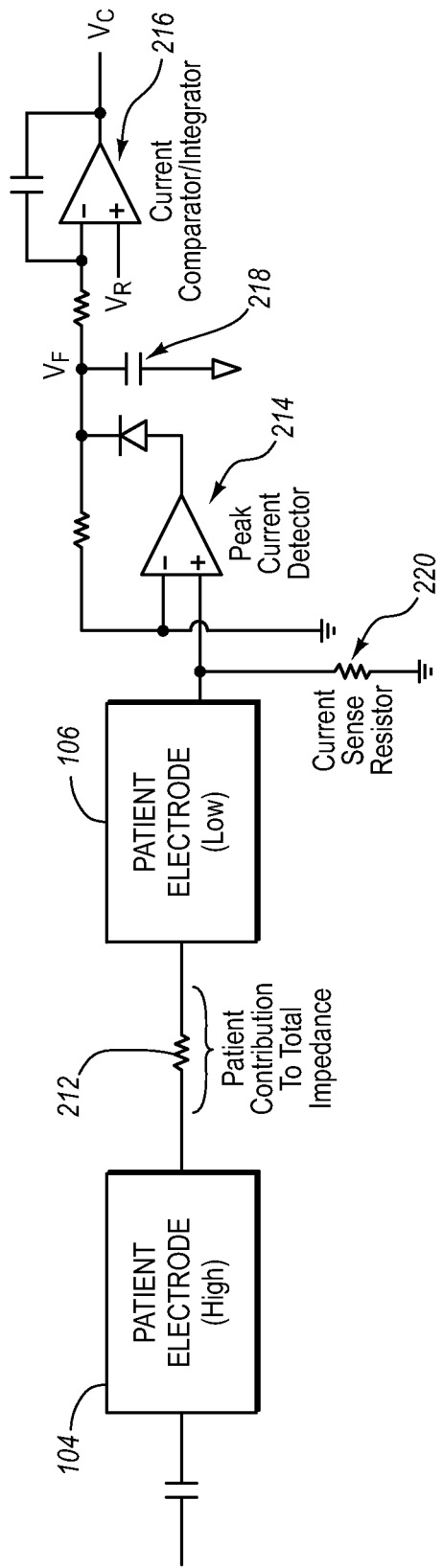

BONE GROWTH STIMULATION USING A CONSTANT CURRENT CAPACITIVELY COUPLED STIMULATOR

This application claim the benefit of U.S. Provisional Application Ser. No. 61/076,991, filed Jun. 30, 2008 and entitled "Bone Growth Stimulation Using a Constant Current Capacitively Coupled Stimulator" and U.S. Provisional Application Ser. No. 61/133,785, filed Jun. 30, 2008 and entitled "Bone Growth Stimulation Using a Constant Current Capacitively Coupled Stimulator", which applications are incorporated by reference in their entirety.

BACKGROUND OF THE INVENTION

1. The Field of the Invention

The present invention relates generally to medical devices and methods of bone growth stimulation. More particularly, the present invention relates to devices, systems, and methods for non-invasive bone growth stimulation using a constant-current capacitively-coupled stimulator.

2. The Relevant Technology

The two most prominent methods of stimulating bone growth across failed unions of fractures of bones are to subject them to an ultrasonic stimulus or an electrical stimulus. Electrical stimulus seems to be the preferred therapy for long bone fractures that have failed to heal. Small and flat bones seem to respond better (or more conveniently) to ultrasonic therapy.

The electrical stimulus of long bone fractures that have failed to respond and heal with conventional therapies, such as fixation, pinning, bone grafts, etc. are divided between two primary methods. The oldest method is pulsed electromagnetic stimulation (PEMS). PEMS requires the area of the fracture to be encased in a fixture containing an electrical coil through which a series of pulsed electrical currents in a rather sharply defined wave pattern are passed. There are many clinical studies that validate the effectiveness of this method of treatment. PEMS usually requires that the patient remain non-ambulatory during each treatment session. The equipment is not very portable and must be carefully size adjusted to each patient application.

The second method of providing electrical bone growth stimulus to long bone fractures is through capacitance coupled electrostatic stimulation (CES). CES treatment requires the placement of two electrodes, typically approximately 30 mm in diameter, in axial alignment with the fracture and in radial opposition to each other across the fracture site. An AC electrical signal is applied to the electrodes.

The CES method of treatment is far more flexible in application than the PEMS method and allows the patient, if otherwise ambulatory, to go about life as usual while undergoing treatment from a portable device that can in many cases weigh less than one pound.

Conventional CES devices use a constant voltage approach. That is, the signal provided to the electrodes is generated such that the voltage remains substantially constant over time, typically at 5 volts, peak-to-peak. In such devices, the current typically fluctuates so as to keep the voltage constant. It appears, through clinical trials, that the most effective electrical signal in a CES system in promoting the healing of a failed long bone fracture appears to be a 60.0 kHz sine wave that delivers between 5.0 and 7.5 milliamps, RMS, to the electrodes. It appears that delivered currents less than 5.0 milliamps, RMS, fail to produce the desired results. Some clinical indications have further shown that currents in excess of 10.0 milliamps, RMS, may cause harm and even some bone death. Thus, to produce a therapeutic benefit, the CES current should fall within the narrow range of between 5.0 milliamps RMS and 10.0 milliamps RMS. As such, there is a need in the art for a CES device that can produce a current to the electrodes that is substantially constant and doesn't vary below 5.0 milliamps or above 10.0 milliamps, RMS.

BRIEF SUMMARY OF THE INVENTION

These and other limitations are overcome by embodiments of the invention which relate to systems and methods for non-invasive bone growth stimulation. Non-invasive bone growth stimulation, for example, can be used in the treatment of non-union fractures. The electrical stimulus of bone fractures, such as long bone fractures, can promote the healing of bone fractures. Embodiments of the invention apply a constant current (e.g, a constant AC current). Applying a constant current source with a bone growth stimulation system delivers a beneficial or therapeutic benefit to a target area, such as a bone fracture.

A bone growth stimulation system can be a constant current device that delivers a constant current to a patient without regard to the impedance presented by the patient. Delivering constant current differs from a constant voltage system (where the current varies to keep voltage constant). In one example, the bone growth stimulation system delivers a constant 7.5 mA RMS to the patient without regard to the impedance until the limit of the available output voltage is reached. This limiting level may be 7.5 Volts (peak-to-peak). Of course, the current design can be altered to increase the available 60 kHz output level to 15.0 Volts (peak-to-peak) (a safe level for human application) while maintaining the constant current level at 7.5 mA (RMS). One of skill in the art can appreciate, with the benefit of the present disclosure, that the specific current delivered to the patient can change. In general, however, the constant current is greater than about 5.0 mA RMS and less than 10.6 mA RMS. In some instance, the bone growth stimulation system is configured to keep the constant current below levels (e.g, 10.0 mA RMS) that may result in adverse results, such as bone death and absorption.

A bone growth stimulator system may include a bone growth stimulator having circuitry that generates an external sinusoidal signal having a substantially constant current. The current is typically a constant AC current. The bone growth stimulator system may also include electrodes electrically connected to the bone growth stimulator and configured to capacitively couple with each other through the body of a person, the sinusoidal signal being received by the electrodes. The bone growth stimulator system may also be capacitively coupled to the bone growth stimulator to prevent DC components from being delivered to the target area.

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter. Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

To further clarify at least some of advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 2C illustrates a pair of low pass filters for generating a sinusoidal signal from a square wave input signal;

FIG. 2D depicts a more detailed diagram of circuitry of the bone growth stimulator illustrated in FIG. 2A including a peak current detector and a current comparator that may be used to determine and ultimately control the constant current delivered to a patient;

DETAILED DESCRIPTION

Figure 1:
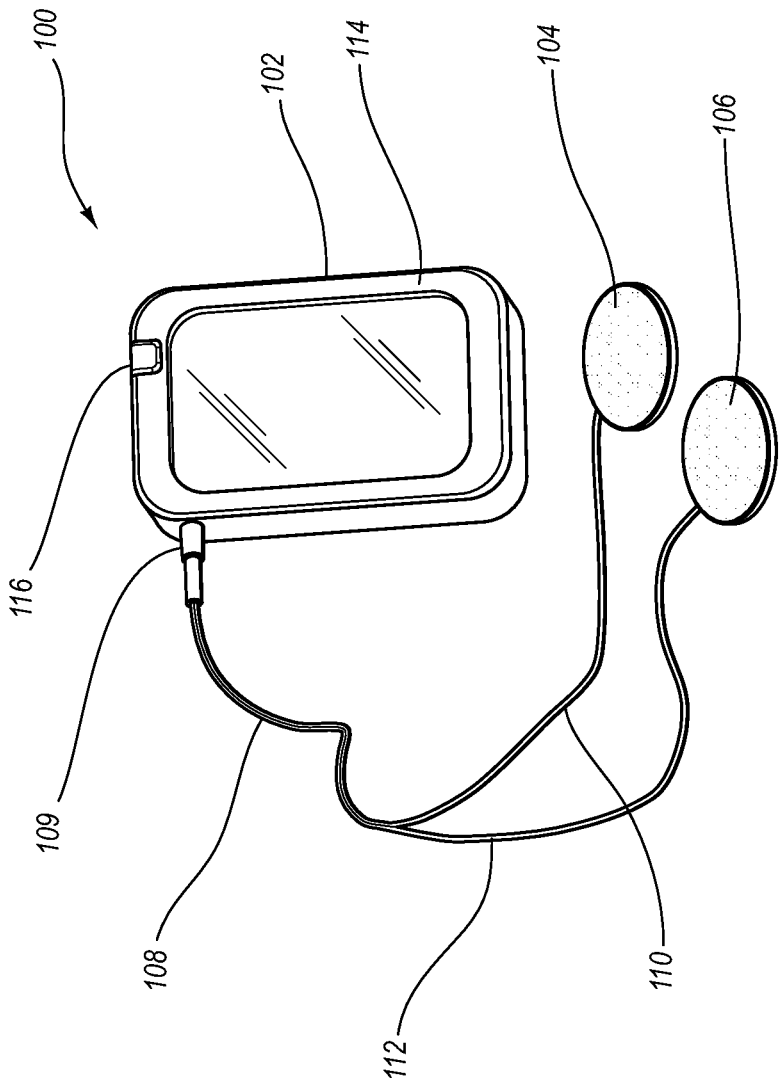
FIG. 1 illustrates one embodiment of a bone growth stimulator system according to the present invention.

The present invention relates generally to medical devices, systems, and methods for non-invasive bone growth stimulation. More particularly, the present invention relates to a constant-current capacitively-coupled stimulator system and its method of use. The medical devices, systems, and methods of the present invention are generally simple to manufacture, easy to use, operable with minimal steps, and reliable during operation and use.

The following discussion will be directed to various configurations of the medical device, system, and method according to the present invention, but it will be understood that the described medical device, system and method are only illustrative embodiments and do not limit the applicability of the general disclosure of the invention to other configurations and embodiments of medical devices, systems and methods that are capable of bone growth stimulation using a constant current capacitively coupled approach.

Embodiments of the invention relate to systems and methods for non-invasive bone growth stimulation. Embodiments of the invention deliver a constant or a substantially constant current to a patient without regard to the patient's impedance. As used herein, constant current typically refers to constant AC current. The current is often selected to assure that the current does not reach a level that can cause bone death and absorption. Further, while some embodiments of the invention are discussed in the context of a 60 kHz signal, other frequencies can be generated and delivered by the bone growth stimulation systems disclosed herein.

An example bone growth stimulation system or bone growth stimulator may operate as a linear current generator with patient/electrode impedances that may range, by way of example only from 0 (zero) ohms to 325 ohms or to 350 ohms. The device may be, by way of example only, a constant current device that will deliver a constant 7.5 mA (RMS) to the patient without regard to the impedance presented by the patient until the limit of the available 60 kHz output voltage is reached. This limiting level may be 7.5 Volts (peak-to-peak). In other words, the bone growth stimulation system delivers a constant current while adjusting the peak-to-peak voltage or control voltage according to the impedance of the patient. This allows the proper constant AC current to be delivered for therapeutic effect and avoids currents that do not provide therapeutic effect or that may cause harm to the patient.

In another embodiment, the peak to peak output level may be increased to as high as 15.0 Volts while maintaining the constant current level at 7.5 mA RMS without risking exceeding the 10.0 mA RMS level that may represent a level that can be counterproductive or harmful to the patient. This results in a constant current bone growth stimulation system that can deliver a constant 7.5 mA (RMS) (or other therapeutic RMS current) to the patient without regard to the impedance presented by the patient until the limit of the available 60 kHz (or other suitable frequency) output voltage is reached. The limit, of course can be changed in some embodiments.

FIG. 1 shows a bone growth stimulator (BGS) system 100 according to one embodiment of the present application. As shown in FIG. 1, BGS system 100 comprises a BGS 102 with a pair of electrodes 104 and 106 electrically connected thereto by one or more electrical wires. BGS system 100 delivers a 60 KHz sinusoidal signal to the electrodes 104 and 106. As previously stated, the frequency of the sinusoidal signal can be altered. In addition, the shape of the signal delivered to the electrodes 104 and 106 may also be altered. Currently a sinusoidal signal is believed to provide the best therapeutic effect, but other waveforms can be generated using appropriate wave generators and/or filters. In these embodiments, the resulting signal provides a constant AC current to the patient.

Instead of a constant voltage signal (typically 5.0 volt (peak-to-peak)) as in conventional stimulators, however, the BGS illustrated in FIG. 1 delivers a substantially constant current signal (typically 7.5 milliamps (RMS), and more generally between 5.0 and 10.6 milliamps (RMS)) to the patient. The substantially constant AC current assures that the current delivered to the patient will not reach the level that may cause bone death and absorption.

In the depicted embodiment, a single wire system 108 connects to and extends from BGS 102. The single wire system 108 connects to BGS 102 through a lead receptacle jack 109. The lead receptacle jack can be removable from BGS 102 or can be integrated within BGS 102. The single wire system 108 then splits out in a Y-type connection to two leads 110 and 112 that respectively connect to electrodes 104 and 106. It is appreciated that other types of wired connections can be used, such as having each wire 110 and 112 connect separately to main body of the BGS 102.

BGS 102, in this embodiment, is a low drain stimulation device that can be carried by a patient during treatment. As such, BGS 102 can be battery powered so as to be portable. Of course other types of power can alternatively be used, such as regular house power or the like, if portability is not an issue. BGS 102 is also typically small and lightweight to aid in its portability. For example, the depicted BGS 102 can weigh only about 230 grams and can be about 82.5 mm×26.5 mm×17.5 mm. Other weights and dimensions are also possible.

BGS 102 generates a treatment signal that is applied to the patient's body via the electrodes 104 and 106. BGS 102 includes an outer housing 114 having control inputs and outputs 116 mounted thereon for the user to control and test the system. For example, control inputs and outputs 116 can be disposed on outer housing 114 for the user to turn BGS 102 on and off, perform a self-test on the device, receive verification of the self-test, etc. To perform a self-test, the BGS 102 may have a "push to test" button. When depressed, this "push to test" button may result in the illumination of an LED when a proper, compliant, treatment signal is being delivered. The LED can be any color, but is usually turned green to indicate a compliant treatment. Other functions or status of the BGS 102 may also be presented to the user visually, for example on a display or using additional LEDs.

The electrodes 104 and 106 are for delivering a signal to the body. For example, the electrodes 104 and 106 depicted in FIG. 1 can be 35 mm diameter, self-adhesive, soft patch, electrodes. Other electrodes can also be used with the benefit of the present disclosure, as is known in the art, of varying dimensions and characteristics. When applying the electrodes 104 and 106 to a patient, the impedance presented to the electrodes 104 and 106 at the long bone fracture sites may vary with the skin-electrode interface, electrode type and bone size and/or surrounding body structure. Using the electrodes 104 and 106 chosen for the BGS system, constant or substantially constant AC current can be delivered to fracture sites. The electrode separation can be up to about 120 mm. Other separation distances are also contemplated as within the scope of the invention.

BGS 102 typically operates as a linear current generator with patient/electrode impedances that range from 0.0 ohms to 325 or to 350 ohms. The BGS delivers an effective patient current up to an electrode separation of 120 millimeters. This is due in part to the fact that the device delivers a nearly constant 7.5 volt (peak-to-peak) output to the patient electrodes when the patient/electrode impedance exceeds 325 Ohms. Above about 325 ohms, however, the current begins to drop and at around 500 ohms impedance the current drops to about 5 milliamps.

Figure 2A:
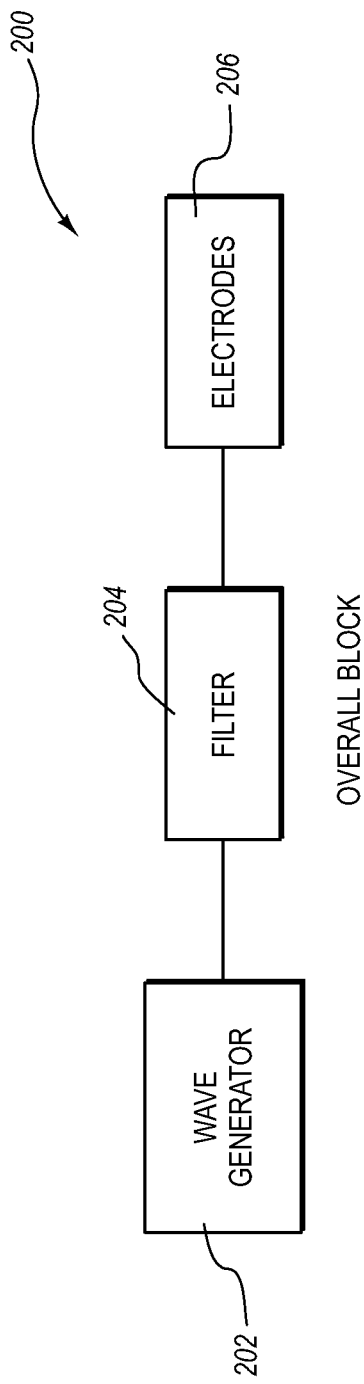
FIG. 2A illustrates a block diagram of one embodiment of a bone growth stimulator system that includes a wave generator and a filter to generate a signal that is provided to the system's electrodes.

Turning to FIGS. 2 and 3, BGS 102 may include a circuit board disposed within outer housing 114 containing electronic circuitry mounted thereon. FIG. 2 illustrates an example BGS system 200, which is one example of the BGS 100. The system 200 typically includes a wave generator 202 (which may be implemented by a microprocessor or other circuitry) that cooperates with a filter 204 to deliver a current source to the electrodes 206 (e.g., electrodes 104 and 106). The wave generator 202 generates a square wave in this example.

Figure 2B:
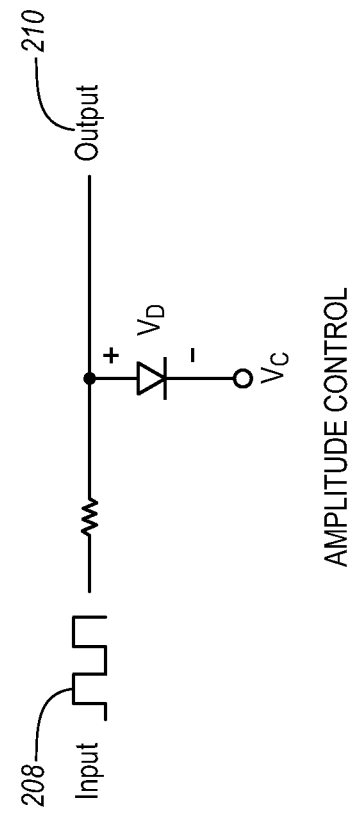
FIG. 2B illustrates a representation of circuitry for controlling an amplitude of an input signal.

The amplitude of a square wave, such as the square wave 208 in FIG. 2B, can be controlled with a DC voltage. In FIG. 2B, the output square wave 210 can be fed into a high impedance (e.g., the non-inverting input of an operational amplifier). The peak-to-peak output voltage can be, in this example, 0.0 Volts to $+V_C+V_D$.

A square wave is typically composed of an infinite series of sine waves and a DC component. Typically, only the fundamental frequency 1.0/T and the odd harmonics of the fundamental frequency are present in the square wave. Embodiments of the invention filter the square wave with the filter 204 to produce a sinusoidal signal that is delivered via the electrodes to the patient as a constant AC current.

In this example, the filter 204 may include multiple filters or cascaded filters. For example, a low pass filter or multiple low pass filters can be designed to attenuate the odd harmonics to a much greater degree than the fundamental frequency.

When the low pass filter is cascaded or buffered with other filters, the output amplitude of the fundamental frequency can be significantly higher than the output amplitude of the third harmonic. This allows the production of a sine wave at the fundamental harmonic with the amplitude controlled by $V_C$. Embodiments of the invention contemplate the generation of a sinusoidal signal having the fundamental frequency and where the harmonic frequencies have been sufficiently attenuated by the filter 204. In one example, the amplitude of the fundamental frequency is about 23 to 24 times greater that the amplitude output of the third harmonic. As previously stated, this allows the generation of a sinusoidal signal at the fundamental frequency with a controllable amplitude.

The filter 204, as illustrated in FIG. 2C by way of example only, illustrates a resistor 232 that is 10 times the value of the resistor 230. Similarly the value of the capacitor 236 is one-tenth the value of the capacitor 234.

As illustrated in FIG. 2D, the output patient current can be controlled at a constant level (e.g., 7.5 mA RMS) by comparing a voltage derived from the peak patient current, $V_F$, to a reference voltage $V_R$, and adjusting $V_C$ to produce the desired result. This is often a continuous process that keeps $V_F = V_R$. This allows the bone growth stimulation system to account for different patient impedances while still providing a constant AC current that has a therapeutic effect.

FIG. 2D illustrates the electrodes 104, 106 that are capacitively coupled to a patient impedance 212. The peak current detector 214 converts the peak current delivered to the patient to a voltage $V_F$ using the capacitor 218. This voltage $V_F$ is then compared by the comparator/integrator 216 to a reference voltage $V_R$. FIG. 2D also illustrates a current sense resistor 220 used in sensing the current delivered to the patient. The value of the current sense resistor 200 is typically known and generates the voltage input to the peak current detector 214. This can then be used to generate the voltage $V_F$ compared to the reference voltage $V_R$.

Advantageously, embodiments of the invention relate to a bone growth stimulator that provides constant AC current from a good sinusoidal signal. As described herein, the sinusoidal signal is generated from a square wave that is converted to a sinusoidal signal using low pass filters. This allows control of the amplitude to deliver constant current and is achieved—not by the gain of a non-linear amplifier (which introduces distortions)—but by generating the sinusoidal signal from a square wave in one embodiment.

FIGS. 3A-3I illustrate schematics for a bone growth stimulator. The electronic circuitry illustrated in FIGS. 3A-3I is used to control and monitor the system as well as provide the constant current signals to electrodes 104 and 106. In the exemplary embodiment, the electronic circuitry includes a microprocessor U1 and/or memory and various digital and analog circuitry portions. The microprocessor U1 performs the compliance monitor functions, such as logging the total continuous minutes of each treatment that is compliant (e.g, no less than 5.0 milliamps RMS) so that it can be downloaded to a clinician's PC. The compliance monitor implemented by the microprocessor U1 can record the relevant information for a clinician. It can record the number and times of compliant treatments, length of treatments, current delivered to patient, malfunctions, and the like or any combination thereof.

In the exemplary embodiment, the constant current sine wave signal used to drive electrodes 104 and 106 is derived from a square wave signal supplied by microprocessor U1 (which can be one embodiment of a wave generator or that can implement a wave generator. Turning to FIGS. 3A through 3I, microprocessor U1 supplies a 60.0 kHz square wave signal ("BGS_60 KHZ") to the analog signal portion of the BGS 102 through R104 to Pin 3 of A$2_A$ ("A2A+"). FIG. 4 illustrates the Pin-out and section usage for the quad op-amps A1-A3 used in the exemplary embodiment.

A$2_A$ may have more gain than the supply voltage (the battery) can allow it to deliver. The result is a square wave with a peak-to-peak amplitude nearly equal to the battery voltage. This square wave ("A2A_OUT") is delivered to R105 where the voltage at the cathode of CR101 will exercise control of the amplitude of the signal delivered to the input of A$2_B$ ("A2B+"). This is a very effective gain control for the system (to deliver a constant current output) rather than trying to control the amplitude of a sine wave further into the amplifier chain.

The output of A$2_B$ ("B") is delivered through C101 to a cascade low pass filter network to produce a 60.0 kHz sine wave at the output of A$2_D$ ("C") that has a peak-to-peak amplitude equal to (0.258)*(peak-to-peak amplitude at the output of A$2_B$). This signal has less than 5% total harmonic distortion. In one configuration the distortion is mostly the third harmonic. The two amplifiers in cascade low pass filter are biased at one half the battery voltage so that neither the positive nor negative peaks of the sine wave can ever be clipped. This can be accomplished, by way of example only, by inserting a 2 plus or minus 4.5 V boost power supply chips between the battery and the amplifiers.

The output of A$2_D$ ("C") is delivered through C107 to the input of the patient driver amplifier, A$3_A$ ("A3−"). This amplifier is biased at one-half the battery voltage, from the output of amplifier A$1_A$ ("VB/2"), and the gain limited (R127/R126) so that it cannot be overdriven into clipping at either the maximum positive or negative excursions of the output.

The output of A$3_A$ ("A3A_OUT") drives the patient electrodes and the current sense resistor, R130, through C108. The current sense signal from R130 is applied to the input of A$1_C$, peak detected in the output, CR104 and C109, and applied to the inverting input of the current error signal integrator, A$1_D$ ("A1D−"). CR102, CR103 and amplifier A$1_B$ generate the 1.50 Volt reference that sets the amplitude of the constant current. This reference voltage is delivered to the non-inverting input of the current error signal integrator A$1_D$ ("D").

The output of the patient current peak detector (CR104, C109) ("BGS_LEVEL") in addition to being applied to the current error integrator is applied to the non-inverting input of amplifier A$3_B$. The output of this amplifier ("A3B_OUT") delivered to an analog-to-digital converter input of the microprocessor. This input is used to log all treatments that deliver patient currents between 5.0 and 7.5 milliamp (RMS) (or between another range such as 5.0 mA and 10.6 mA by way of example only) for the compliance monitor function. The same signal is compared to the current reference signal at the output of A$1_B$ in amplifier A3 to provide an on-demand indication of a compliant treatment to the patient, via SW101 and LED101.

Figure 3A:
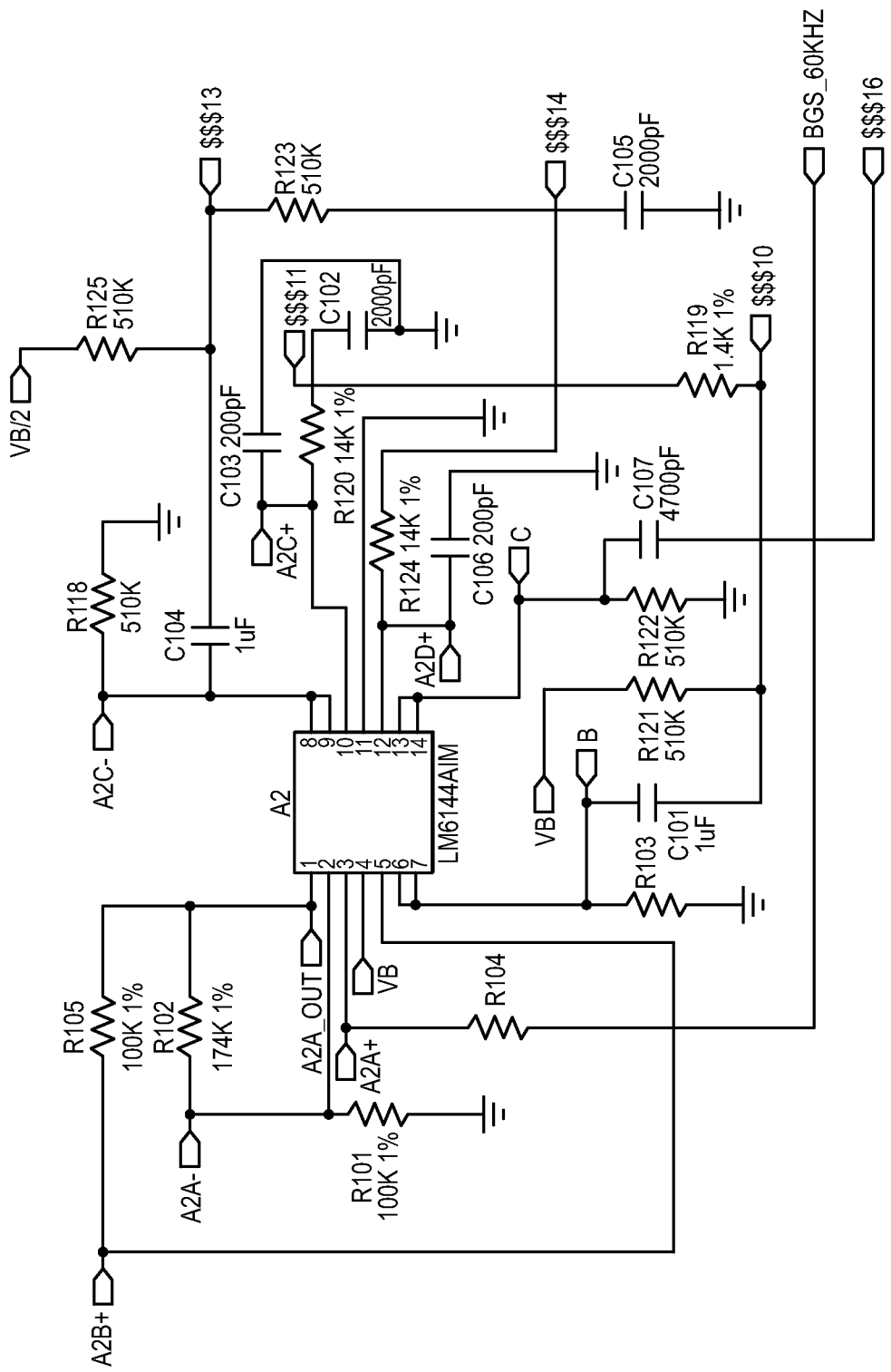
FIGS. 3A-3I illustrate a schematic representation of the circuitry used in one embodiment of the bone growth stimulator according to the present invention.
Figure 3B:
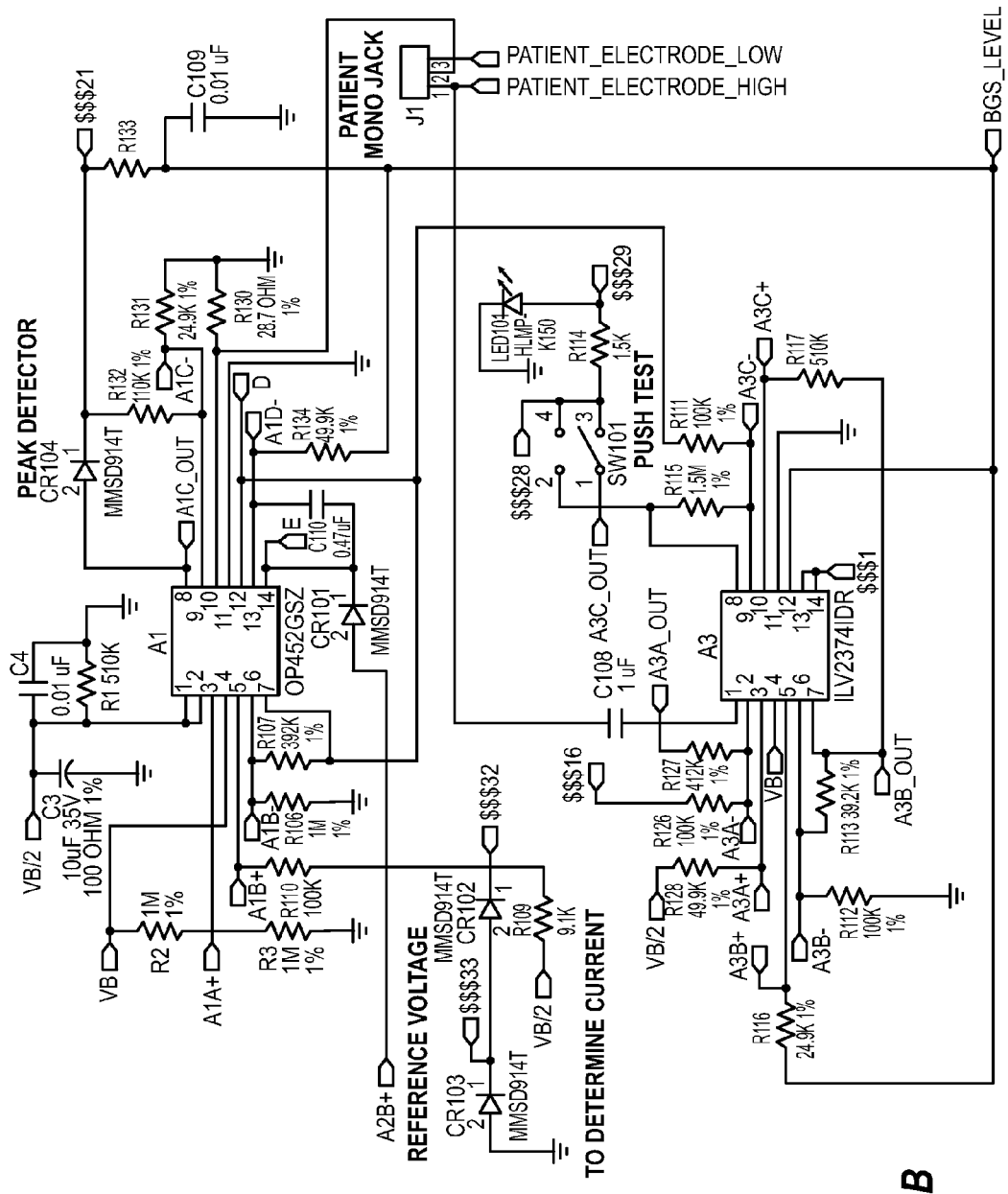
Figure 3C:
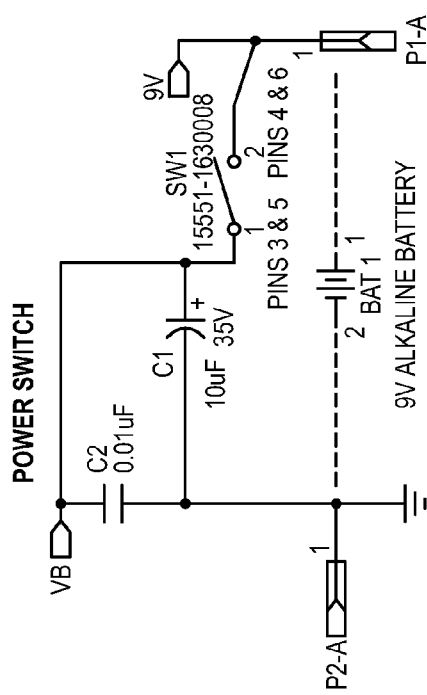
Figure 3D:
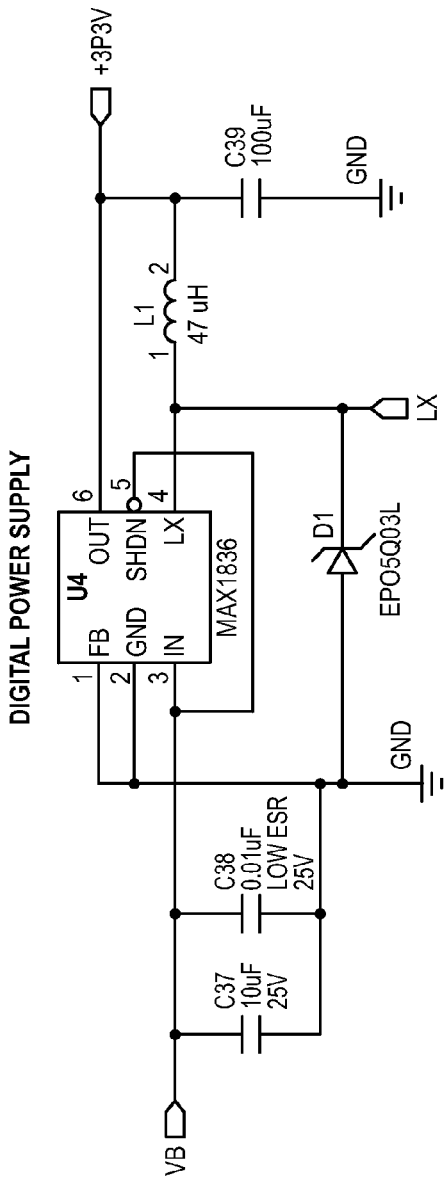
Figure 3E:
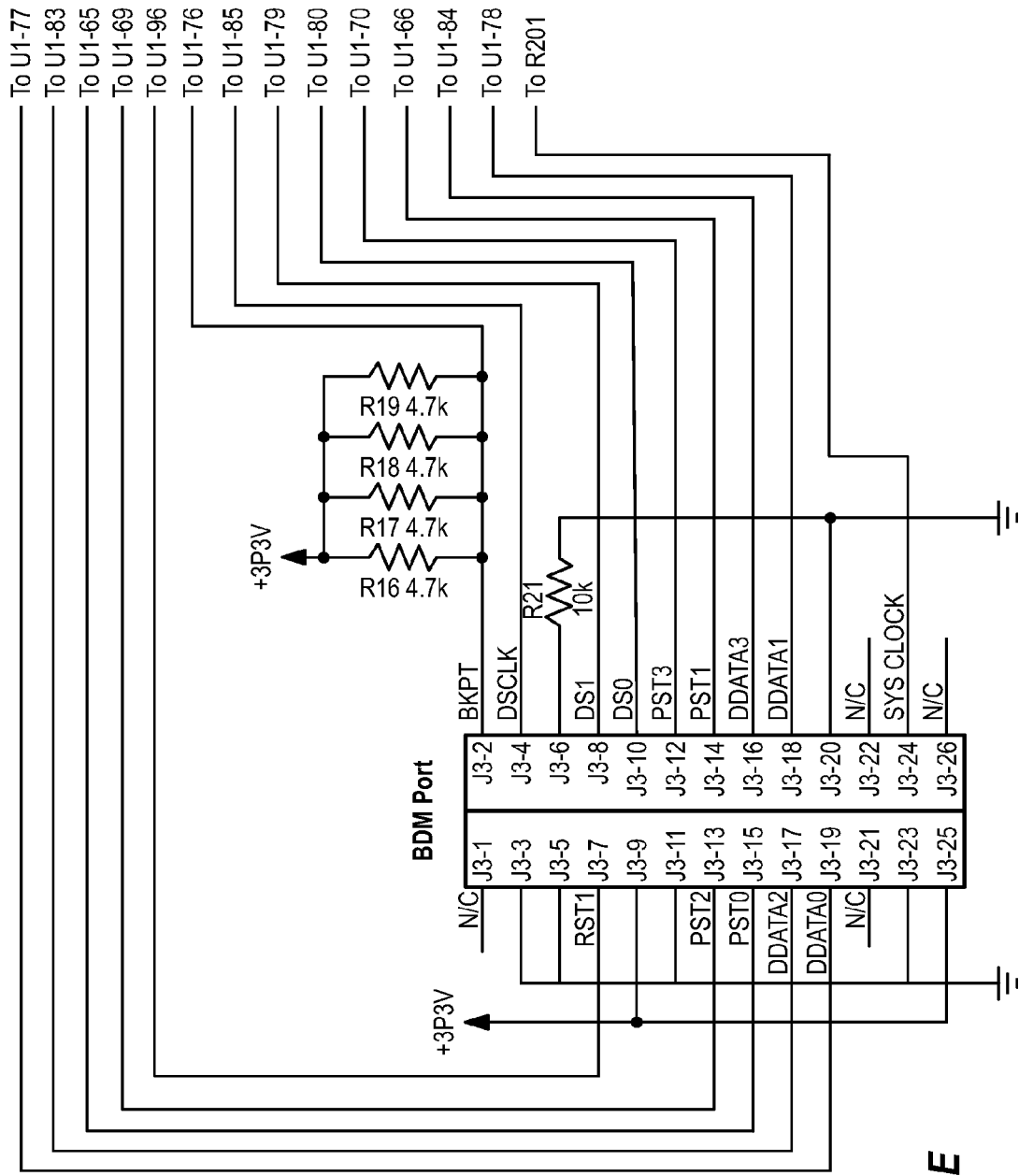
Figure 3F:
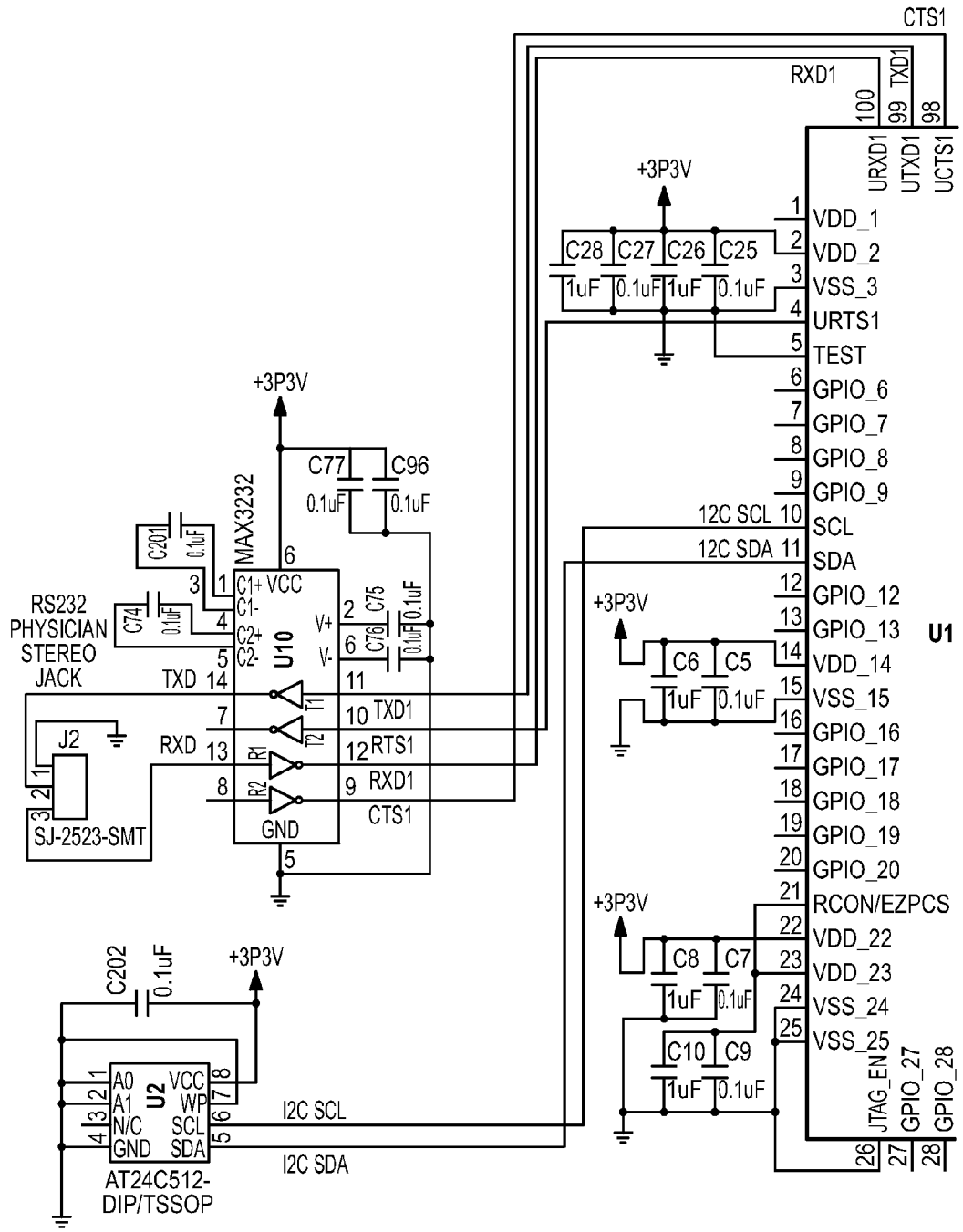
Figure 3G:
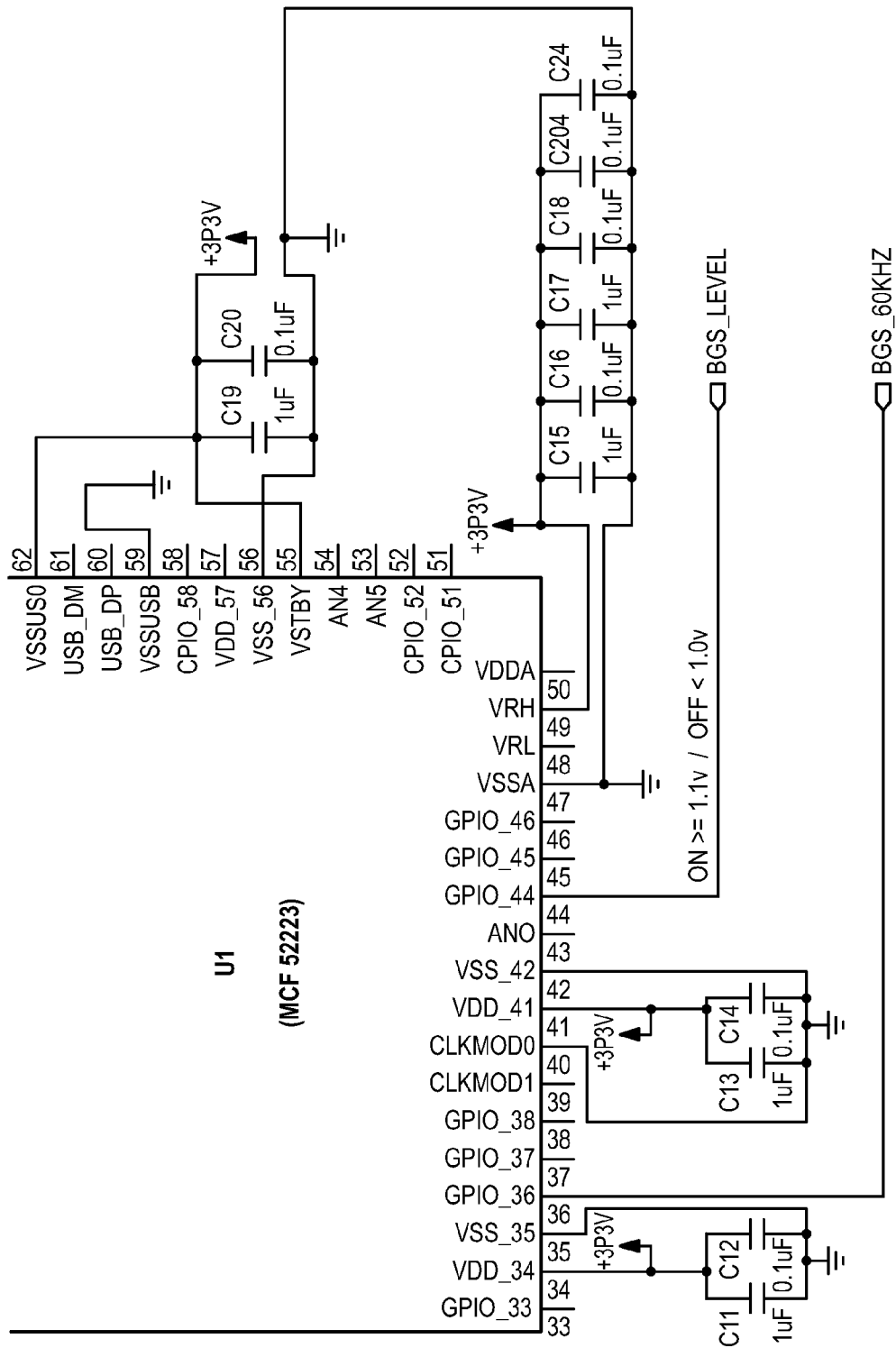
Figure 3H:
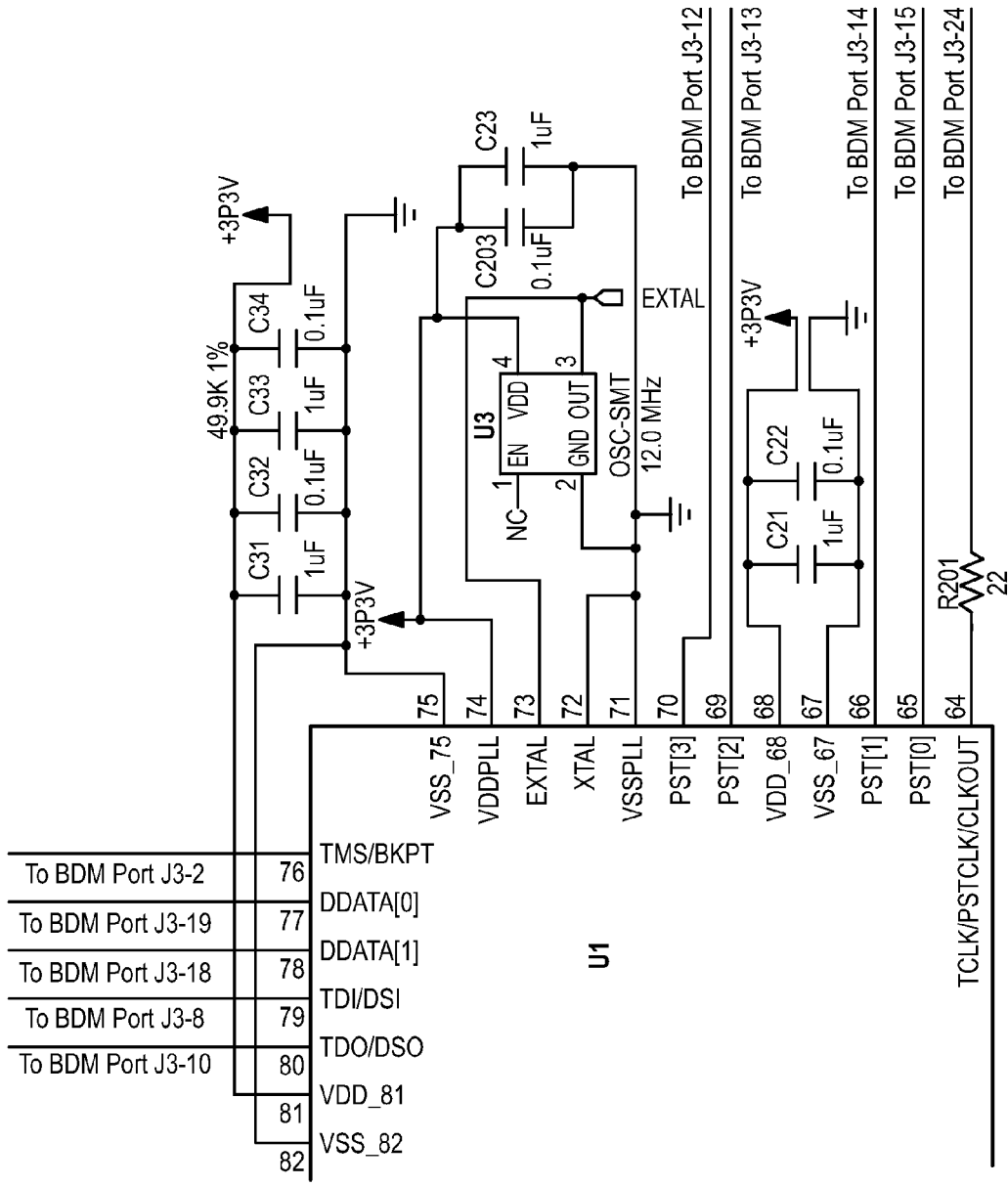
Figure 3I:
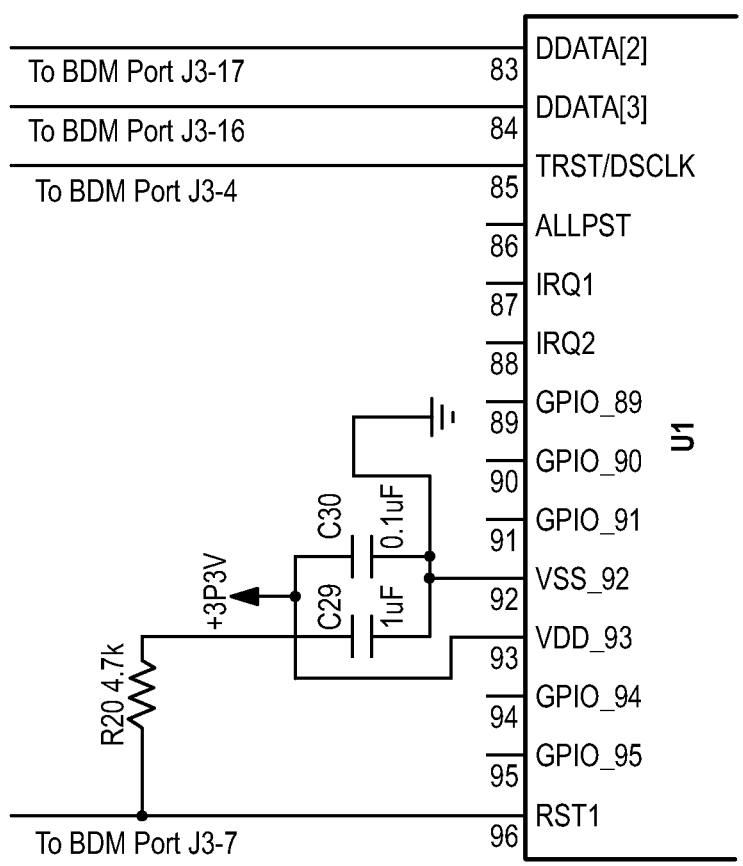
Figure 4:
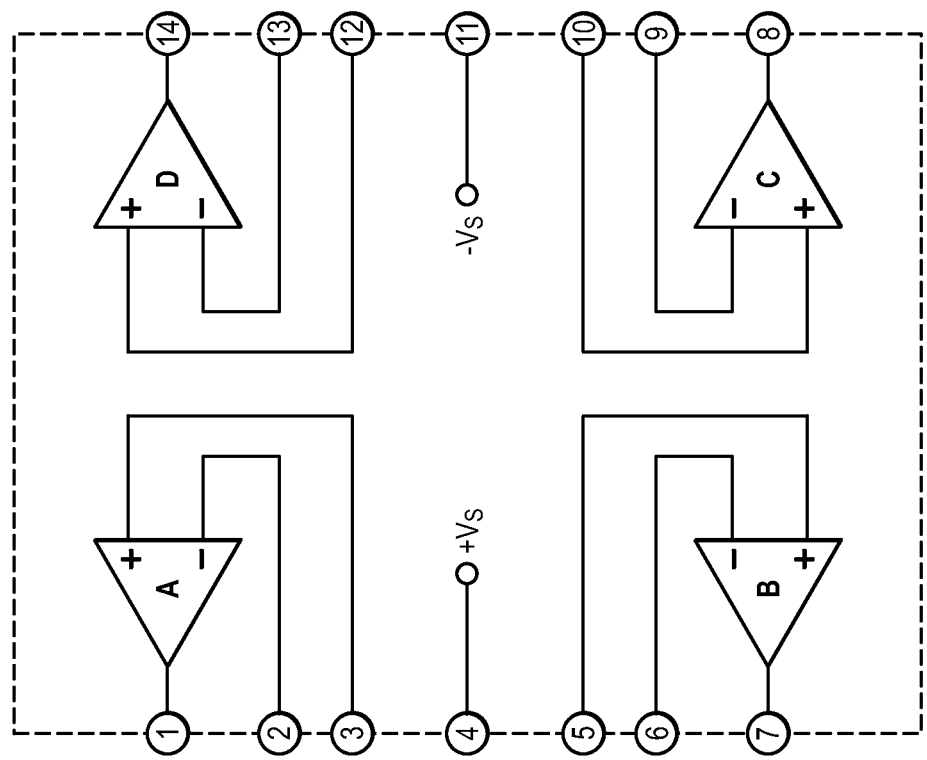
FIG. 4 depicts the pin-out and section usage of quad op-amps used in the circuitry shown in FIGS. 3A-3I.

FIG. 3C illustrates a power switch that can turn the bone growth stimulator on and off when a battery is installed. FIG. 3D depicts a digital power supply. FIG. 3E illustrates a port that can be used to interface the bone growth stimulator with an external device. FIGS. 3F-3I illustrate the signals connected with the microprocessor U1 in the context of FIGS. 3A-3I.

Although the sine wave in the depicted embodiment utilizes a square wave generated by microprocessor U1 as detailed above, it is appreciated that the sine wave can be derived in other known ways in the art. For example, a square wave can be used that is generated by some other circuitry than microprocessor U1. Alternatively, the sine wave can be generated by some process other than beginning with a square wave, as is known in the art.

Figure 5B:
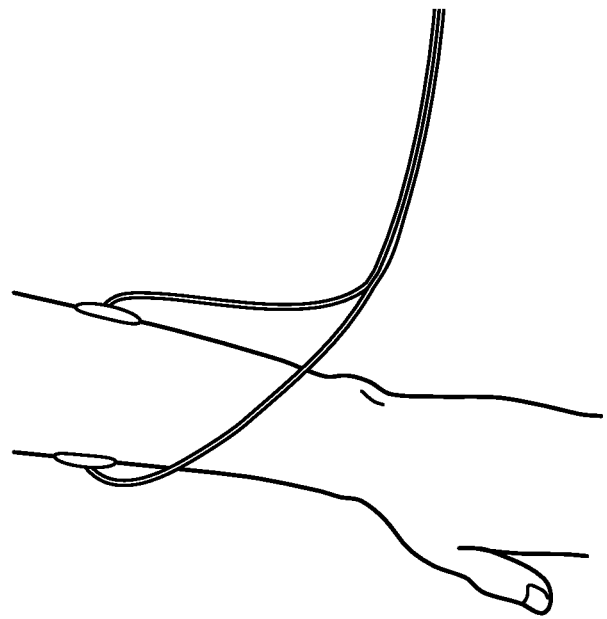
FIGS. 5A-5B illustrate ways in which to attach the electrodes to the body of a person according to one embodiment.
Figure 5A:
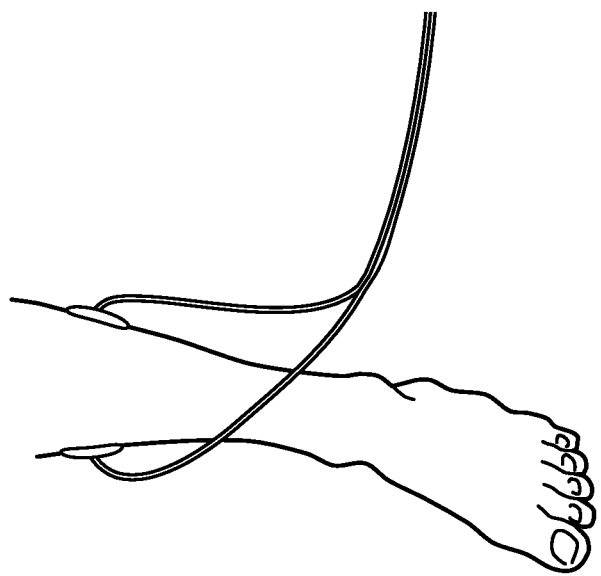

It is also appreciated that more than two electrodes can also be used with the BGS 102 if desired. This may alter the current pattern delivered to a target area. BGS System 100 can also include a carrying case to hold the BGS 102 during treatment and can be worn by the patient over the shoulder, around the waist, around the chest, around an arm or leg or any other configuration that is comfortable for the patient as long as the electrode lead wires are safely secured. A storage case can also be included. The storage case typically holds the BGS 102, spare electrodes 104, 106, and leads, spare batteries and the carrying case when not in use An exemplary method of using the BGS system 100 will now be given. BGS system 100 is used to provide a constant current signal across a broken bone to stimulate bone growth. As shown in the examples of FIGS. 5A and 5B, electrodes 104 and 106 are placed on the patient's skin over the fracture site, with one electrode placed on either side of the limb in this example. Although FIGS. 5A and 5B respectively depict the electrodes being placed on the leg and arm respectively, it is appreciated that other portions of the body can be used. Furthermore, though the discussion herein is directed toward use of the BGS system on a human, the BGS system can also be used for bone growth stimulation on non-human animals, such as dogs, horses, etc.

As shown in FIGS. 5A and 5B, the electrodes are axially aligned with the fracture and in radial opposition to each other across the fracture site. The objective is to provide the shortest physical/electrical path from one electrode, through the fracture to the opposite electrode so as to provide the proper capacitive coupling for therapeutic benefit. The placement of the electrodes may also depend on the fracture type. Alternatively, multiple electrodes may be attached, by way of example only, for specific fracture types.

Referring to FIG. 1, to connect the electrodes 104 and 106: Connect one end of each of the leads 110 and 112 to the electrodes; Connect the other end of the wire system 108 (or each lead, if the leads connect directly to the BGS) to the BGS lead receptacle jack 109; and Connect the BGS lead receptacle jack 109 to the BGS 102 (if needed).

In the exemplary embodiment, the BGS is non-polarized. That is, either electrode may be connected to either lead. In other embodiments, the electrodes may be polarized.

Once the electrodes 104 and 106 are properly positioned on the patient and the leads 110 and 112 are properly connected to the unit 102, the device is turned "on," such as by pressing an on/off rocker switch or other switching mechanism on the device. In one embodiment, the device is intended for continuous usage, and can be worn by the patient during most normal activities.

Once the device 102 is turned on, the system can be tested by performing a self-test. To do this, the user presses a button or the like, which signals the user if the unit is functioning correctly, such as by a light (e.g., a green LED or other color or indicator) or audio signal or the like. Alternatively, the signal can be actuated if the unit is not functioning correctly.

When turned on and correctly attached to the patient, the BGS 102 sends a sinusoidal constant current signal of between 5 and 7.5 (but can be higher, e.g., as high as 10.6 or more) milliamps (RMS) to electrodes 104 and 106, which are capacitively coupled through the patient. The constant current signal passes through the damaged bone structure (or other tissue) and aids in bone growth stimulation. The constant current signal is allowed to continue for a predetermined period of time, as directed by a doctor. During this time, the signal remains between 5.0 and 7.5 milliamps RMS.

To discontinue use, the BGS 102 is turned off by pressing the on/off rocker switch or another switch or the like. The electrodes 104 and 106 are then removed from the patient. The BGS System 100 can be used a single time or a series of times, according to the directions of the doctor.

The present invention may be embodied in other specific forms without departing from its spirit or essential characteristics. The described embodiments are to be considered in all respects only as illustrative and not restrictive. Additional embodiments and inventions are described in the attached Exhibits, which are attached hereto and incorporated herein by reference.

The invention claimed is:

1. A bone growth stimulator system configured to stimulate bone growth in a body, the bone growth stimulator system comprising:
    a bone growth stimulator having circuitry that generates a signal, wherein the bone growth stimulator adjusts a voltage of the signal to account for changes in an impedance of the body such that a substantially constant current is delivered while the bone growth stimulator:
        is attached to the body, and
        stimulating the bone growth;
    a filter that filters the signal to produce a sinusoidal signal having a particular frequency, wherein other frequencies in the signal are substantially filtered, wherein an amplitude of the sinusoidal signal is controlled with a control voltage, the circuitry adjusting the voltage of the generated signal to control the amplitude of the sinusoidal signal to maintain the substantially constant current as the impedance of the body changes, wherein the sinusoidal signal is configured to stimulate bone growth;
    wherein the circuitry senses a current delivered through the body and adjusts the voltage of the generated signal by comparing a sensed voltage generated from the sensed current with a reference voltage to produce the control voltage, wherein the control voltage is used by the circuitry to adjust the voltage in order to maintain the substantially constant current;
    a push-to-test button that indicates that the substantially constant current is compliant, wherein the substantially constant current is compliant when the substantially constant current is greater than about 5.0 mA RMS and less than 10.6 mA RMS; and
    electrodes electrically connected to the bone growth stimulator and configured to capacitively couple with each other through a body, wherein only the sinusoidal signal is delivered to the body through the electrodes,
    wherein the circuitry adjusts the voltage to control the amplitude of the sinusoidal signal to account for the changes in the impedance of the body,
    wherein the circuitry includes a processor and is further configured as a compliance monitor to record a number of compliant treatments, a length of each compliant treatment, and whether the substantially constant current is compliant.

2. The bone growth stimulator system according to claim 1, wherein the substantially constant current comprises a substantially constant AC current between 5.0 milliamps RMS and 10.6 milliamps RMS.

3. The bone growth stimulator system according to claim 1, wherein the sinusoidal signal is generated from a square wave.

4. The bone growth stimulator system according to claim 3, wherein the circuitry comprises a wave generator that generates the square wave.

5. The bone growth stimulator system according to claim 3, wherein the filter generates the sinusoidal signal from the square wave.

6. The bone growth stimulator system according to claim 5, wherein the filter comprises cascaded low pass filters to isolate the particular frequency of the square wave while attenuating odd harmonics of the square wave to a greater degree than the particular frequency.

7. The bone growth stimulator system according to claim 1, wherein the sinusoidal signal has a frequency of about 60 kiloHertz.

8. The bone growth stimulator system according to claim 1, wherein the circuitry comprises a microprocessor that adjusts the voltage to ensure that the sinusoidal signal has a substantially constant AC current.

9. The bone growth stimulator system according to claim 8, wherein the circuitry comprises:
    a peak detector that derives a first voltage from a peak current of the substantially constant current; and
    a comparator that compares the first voltage with the reference voltage to generate a control voltage, wherein the control voltage is adjusted to control the amplitude and produce a desired constant AC current.

10. The bone growth stimulator system according to claim 9, wherein the electrodes are spaced on the body a distance that is less than 120 millimeters.

11. The bone growth stimulator system according to claim 9, wherein the electrodes are axially aligned with a fracture and in radial opposition to each other across the fracture site.

12. The bone growth stimulator system according to claim 1, wherein the substantially constant current is compliant when the substantially constant current is about 7.5 mA RMS.

13. A method of bone growth stimulation, the method comprising:
    attaching electrodes to a body to capacitively couple the electrodes through the body;
    generating a signal;
    filtering the signal with a filter to produce a sinusoidal signal from the generated signal, wherein other frequencies are substantially attenuated by the filter, wherein the sinusoidal signal is configured to stimulate bone growth;
    sensing a current delivered to the body through the capacitively coupled electrodes;
    detecting a peak current value of the current delivered to the body, wherein the peak current value is converted to a sensed voltage;
    comparing the sensed voltage generated from the sensed current with a reference voltage to generate a control voltage;
    adjusting the control voltage to achieve a particular level for a substantially constant AC current, wherein the particular level of the substantially constant AC current is between about 5.0 mA RMS and about 10.6 mA RMS;
    wherein the control voltage is used to adjust a voltage of the signal in order to adjust an amplitude of the sinusoidal signal based on the comparison of the sensed voltage generated from the sensed current and the reference voltage to maintain the substantially constant AC current at the particular level, wherein adjusting the amplitude of the signal accounts for changes in an impedance of the body while:
        the electrodes are attached to the body, and
        the current is delivered to the body for a period of time;

passing only the sinusoidal signal between the electrodes for the period of time, the sinusoidal signal having the substantially constant AC current throughout the period of time; and monitoring a number of compliant treatments to the body, and a length of each compliant treatment, wherein the current is further monitored to ensure that the current delivered to the body is substantially constant during the period of time.

14. The method according to claim 13, wherein generating the signal comprises generating a square wave.

15. The method according to claim 14, wherein generating a signal further comprises attenuating odd harmonics of the square wave to a greater degree than a fundamental frequency of the square wave with the filter.

16. The method according to claim 15, wherein generating a signal further comprises generating the sinusoidal signal such that the sinusoidal signal has a frequency of about 60 kHz.

17. The method according to claim 13, wherein the particular level is about 7.5 mA RMS.

18. The method according to claim 13, wherein the substantially constant AC current is independent of an impedance of the body.

19. The method according to claim 13, further comprising providing an indicator indicating that the substantially constant AC current is compliant with a specified treatment.

20. The method according to claim 13, further comprising storing a number and times of compliant treatments performed to monitor patient compliance with the treatment.

* * * * *